United States Patent [19]

Bakels

[11] Patent Number: 4,787,751
[45] Date of Patent: Nov. 29, 1988

[54] BONE CEMENT MIXING DEVICE

[76] Inventor: Marinus Bakels, 3896 Burns Rd., Palm Beach Gardens, Fla. 33410

[21] Appl. No.: 876,839

[22] Filed: Jun. 20, 1986

[51] Int. Cl.⁴ .................. B01F 11/00; B01F 13/06
[52] U.S. Cl. .................... 366/110; 366/114; 366/124; 366/139; 366/208
[58] Field of Search ............ 366/110, 114, 115, 124, 366/212, 208, 209, 108, 139, 219, 240; 128/92 VQ

[56] References Cited

U.S. PATENT DOCUMENTS

| | | | |
|---|---|---|---|
| 2,247,978 | 7/1941 | van Arkel | 366/110 |
| 2,875,989 | 3/1959 | Toulmin, Jr. | 366/114 |
| 3,061,280 | 10/1962 | Kraft et al. | 366/110 |
| 3,640,510 | 2/1972 | Lea | 366/139 |
| 3,944,188 | 3/1976 | Parker et al. | 366/110 |
| 4,277,184 | 7/1981 | Solomon | 366/139 X |
| 4,522,500 | 6/1985 | Hyer | 366/114 X |
| 4,604,029 | 8/1986 | Fink | 366/124 X |

FOREIGN PATENT DOCUMENTS 4535517 11/1970 Japan ................. 366/139

Primary Examiner—Harvey C. Hornsby
Assistant Examiner—Scott J. Haugland
Attorney, Agent, or Firm—Jack N. McCarthy

[57] ABSTRACT

A bone cement mixing device has a holding chamber mounted in a housing for vibration with its top extending through the top of said housing. A nitrogen operated vibrator vibrates said holding chamber and the interior of said chamber is connected to a vacuum source. A gun cartridge is placed in said holding chamber to receive bone cement ingredients to be vibrated and placed under a vacuum to deaerate the combined ingredients.

10 Claims, 5 Drawing Sheets

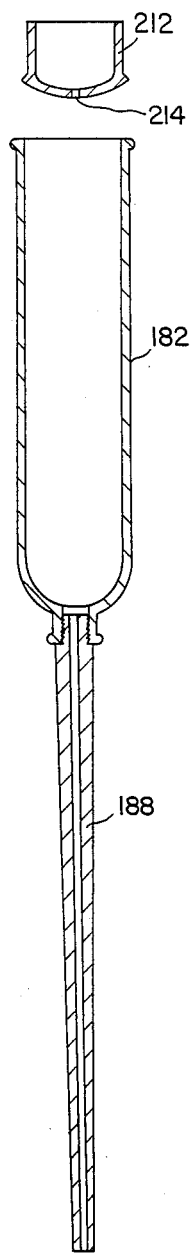
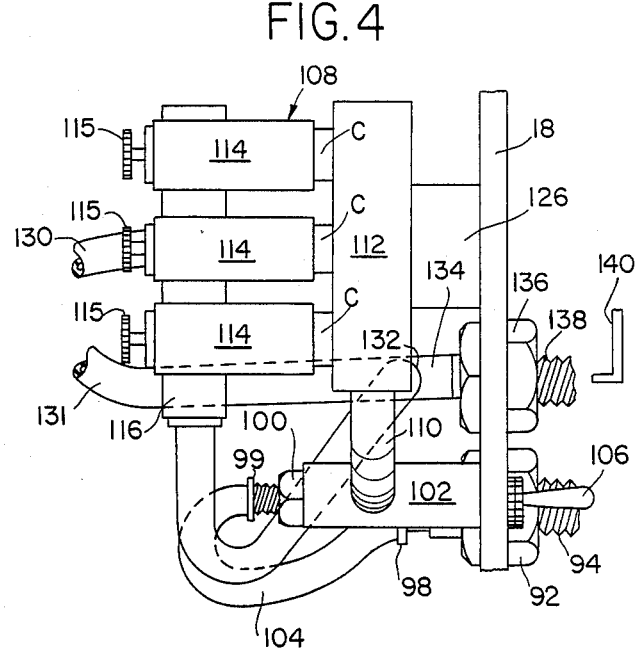
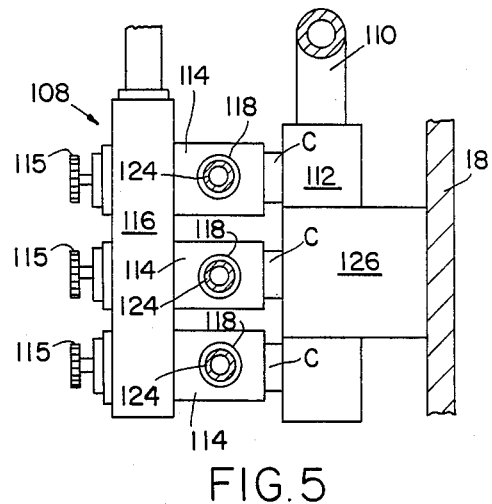

4,787,751

BONE CEMENT MIXING DEVICE

TECHNICAL FIELD

This invention relates to the preparation of bone cement to reduce porosity and improve the fatigue strength of the bone cement, and provide a simplified method of applying the bone cement.

BACKGROUND ART

Bone cement has been prepared generally by mixing the required components, attempting to deaerate the bone cement, and placing it in a bone cement gun for delivery to a desired operating area. Various mixing procedures have been used, including hand-mixing in a bowl with a fume evacuator; and a cement cartridge with the mixed bone cement placed therein has been located in a centrifuge to attempt to reduce porosity. The majority of bone cement guns used are similar and can be used with applicant's apparatus.

DISCLOSURE OF INVENTION

An object of the present invention is to provide a device which will permit the mixing of the bone cement in a cement gun cartridge positioned in a housing, and deaerate the bone cement in the gun cartridge without removing it from the housing.

A further object of the device is to provide a bone cement gun cartridge holding chamber having a vacuum connection for withdrawing fumes therefrom as the bone cement is being mixed by a mixing rod or spatula, to prevent the fumes from entering the operating room.

Another object of the device is to provide a bone cement gun cartridge holding chamber with an enlarged cylindrical projection extending through an opening in the top of said housing having a cover to allow the mixed bone cement to be placed under a vacuum while a vibrator shakes the holding chamber and gun cartridge to deaerate the mixed bone cement. A cover can be used having a rotatable mixing rod with a hand crank on the outside.

A further object of the invention is to provide a rotary vibrator with an eccentric weight to do the vibrating connected to said holding chamber, said rotary vibrator being rotated by a flow of nitrogen from an inlet conduit over a driving turbine; said nitrogen exhausting into an outlet conduit which carries the nitrogen from the housing to a remote location from the surgery for exhaust.

Another object of the invention is to provide an "on-off" actuator on a panel for controlling the vacuum, and an "on-off" actuator adjacent thereto for controlling nitrogen flow to the vibrator.

A further object of the device is to provide a bone cement gun cartridge holding chamber fixed to a mounting plate, said mounting plate being connected to the bottom plate of the housing by shock mounts.

Another object of the invention is to provide a simplified, safe, bone preparation apparatus for an operating room having only one powered part and excluding the use of electricity.

A further object of the invention is to provide regulating means for the nitrogen flow to the turbine vibrator to control the amount of vibration. Other control means regulates the desired amount of vacuum.

BRIEF DESCRIPTION OF THE DRAWINGS

FIG. 4 is a fragmentary top view of the nitrogen circuit shown in FIG. 2;

FIG. 5 is a fragmentary view taken on the line 5—5 of FIG. 2 under the nitrogen regulator device;

FIG. 7 is a view showing the cement gun cartridge with an elongated nozzle fixed to a small opening at one end and a piston member of a bone cement gun which is adapted to be pressed into the cement gun cartridge.

BEST MODE FOR CARRYING OUT THE INVENTION

Figure 1:
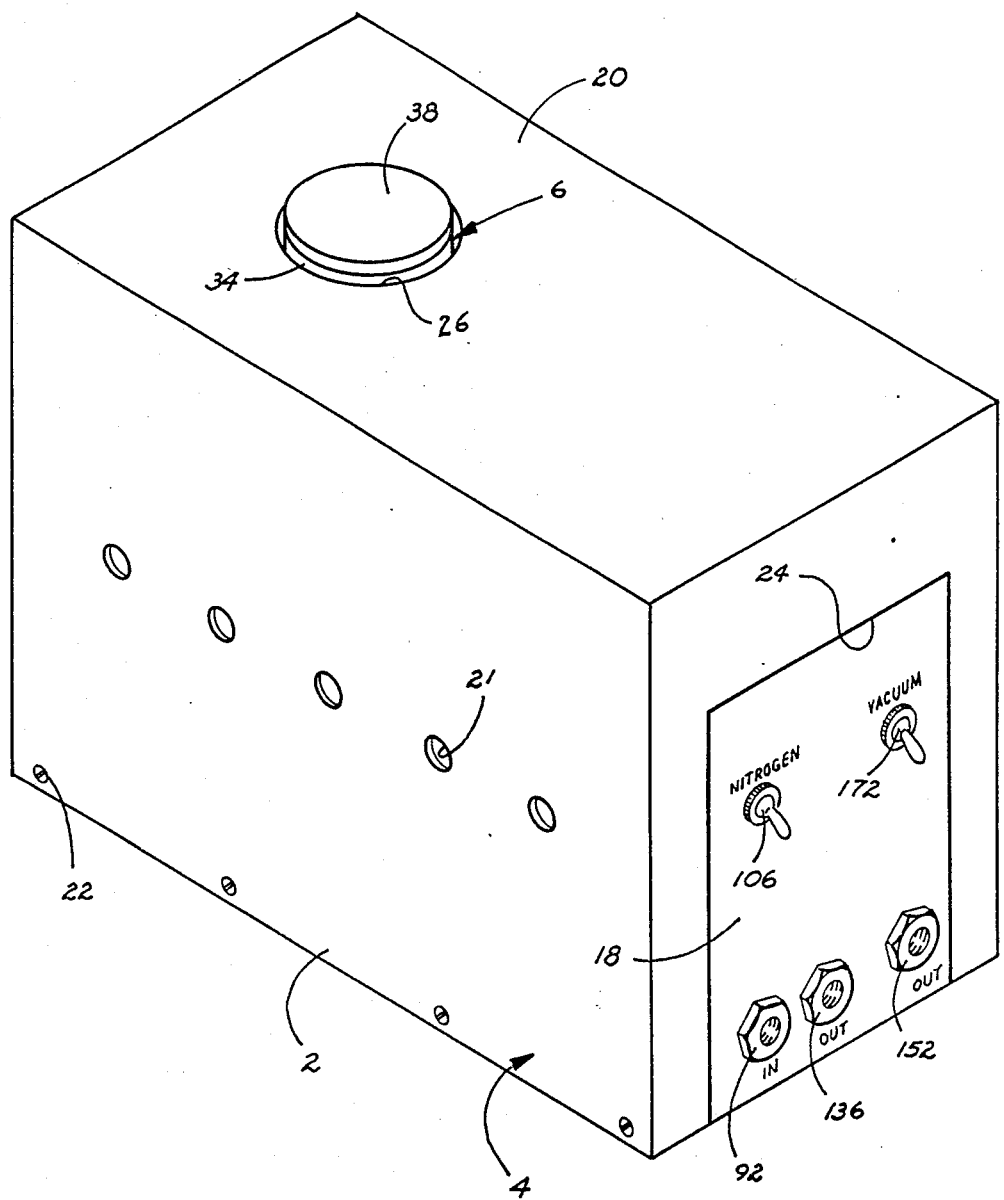
FIG. 1 is a perspective view of the bone cement mixing device for the preparation of bone cement showing nitrogen and vacuum controls and connections.
Figure 2:
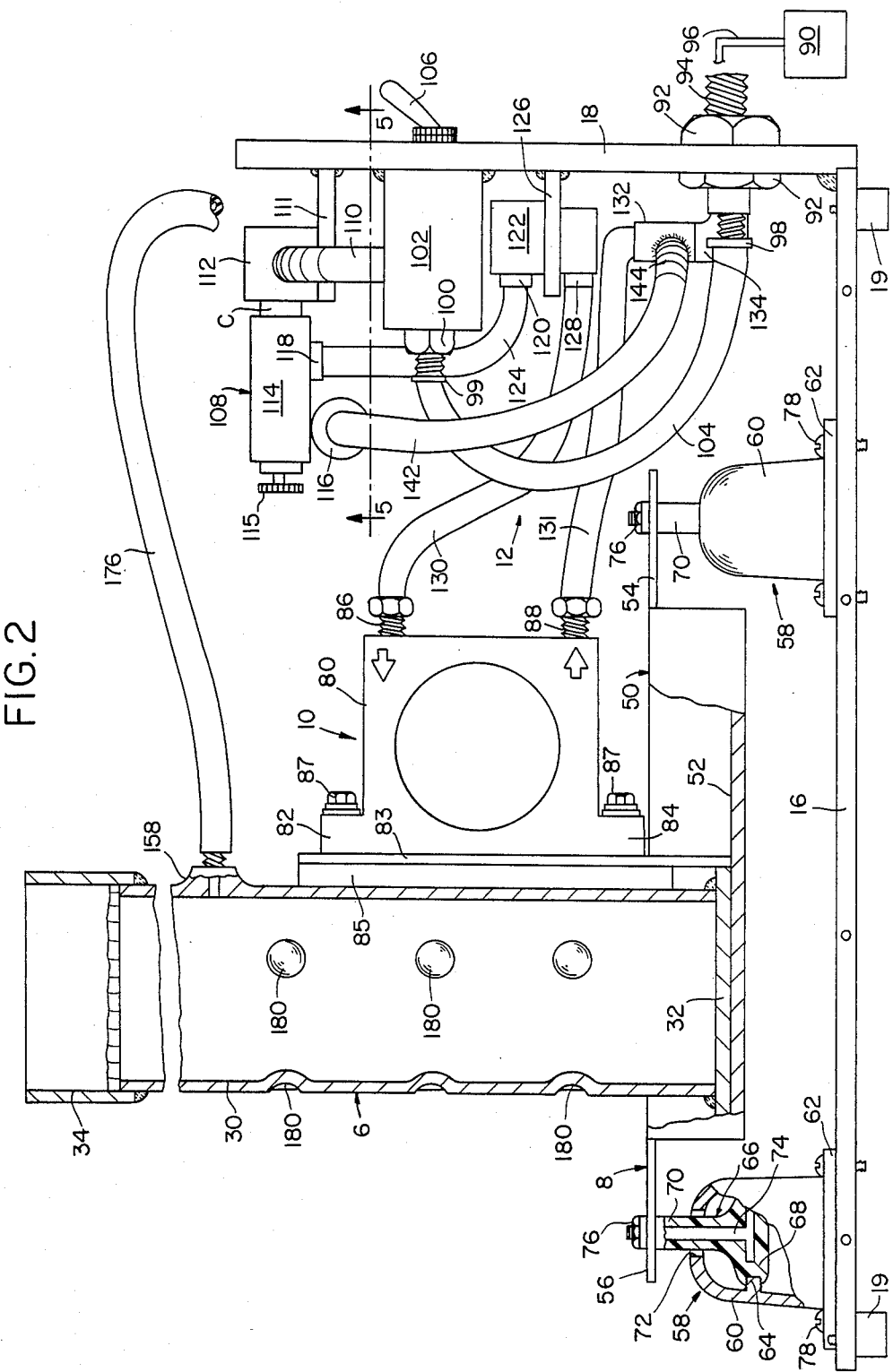
FIG. 2 is a left side view of the bone cement mixing device omitting the housing cover and the vacuum circuit, and showing the bone cement holding chamber and a portion of the mounting means in section.
Figure 3:
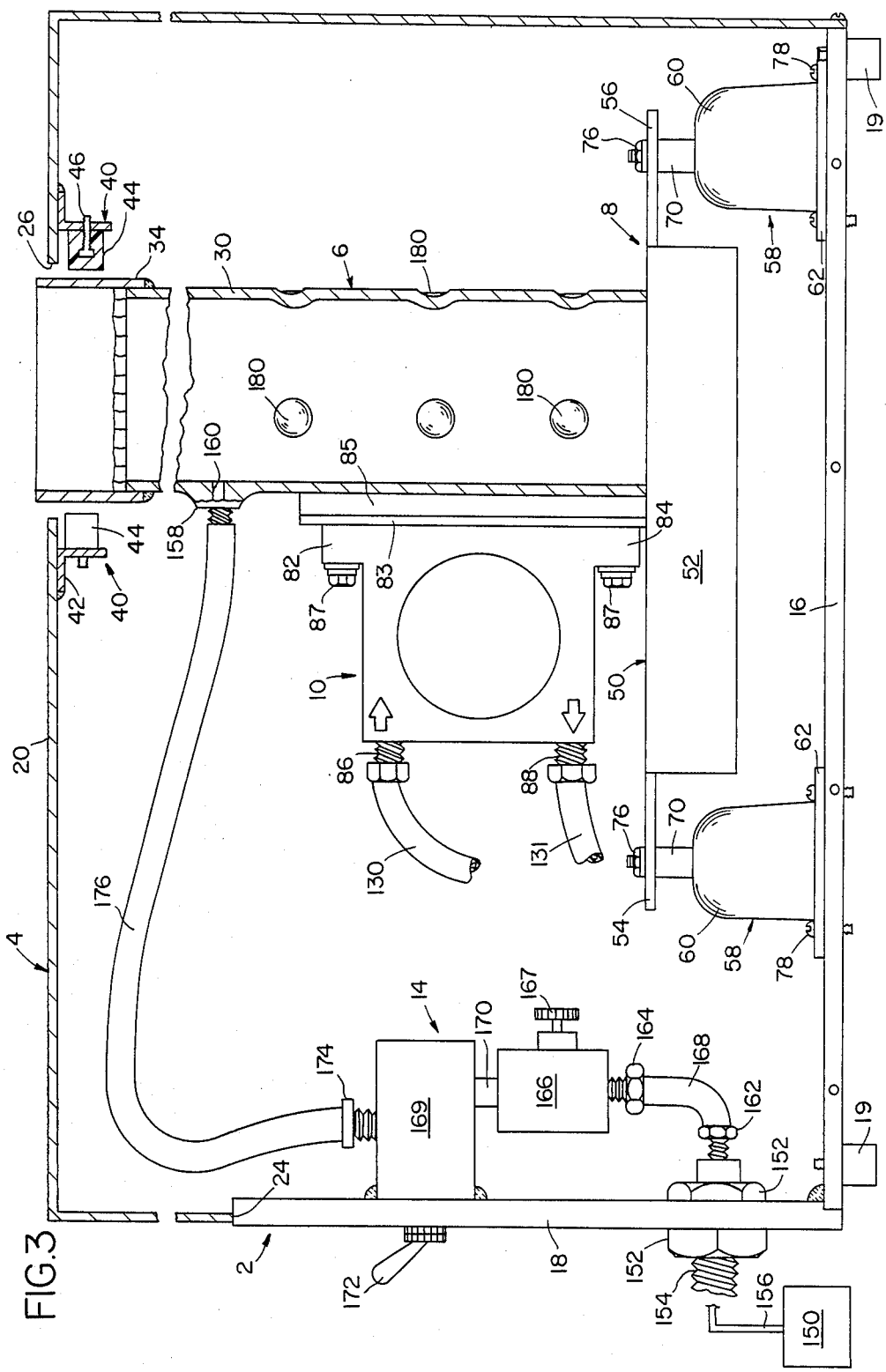
FIG. 3 is a right side view of the bone cement mixing device omitting the nitrogen circuit and showing the housing cover and bone cement holding chamber in section.
Figure 8:
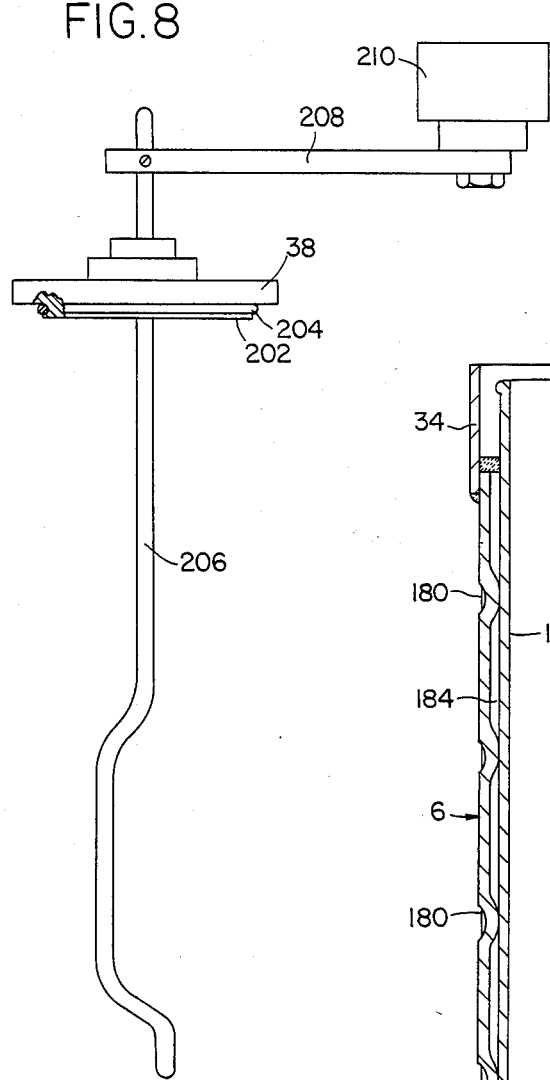
FIG. 8 is a view of a cartridge holding chamber cover with a rotatable mixer.
Figure 6:
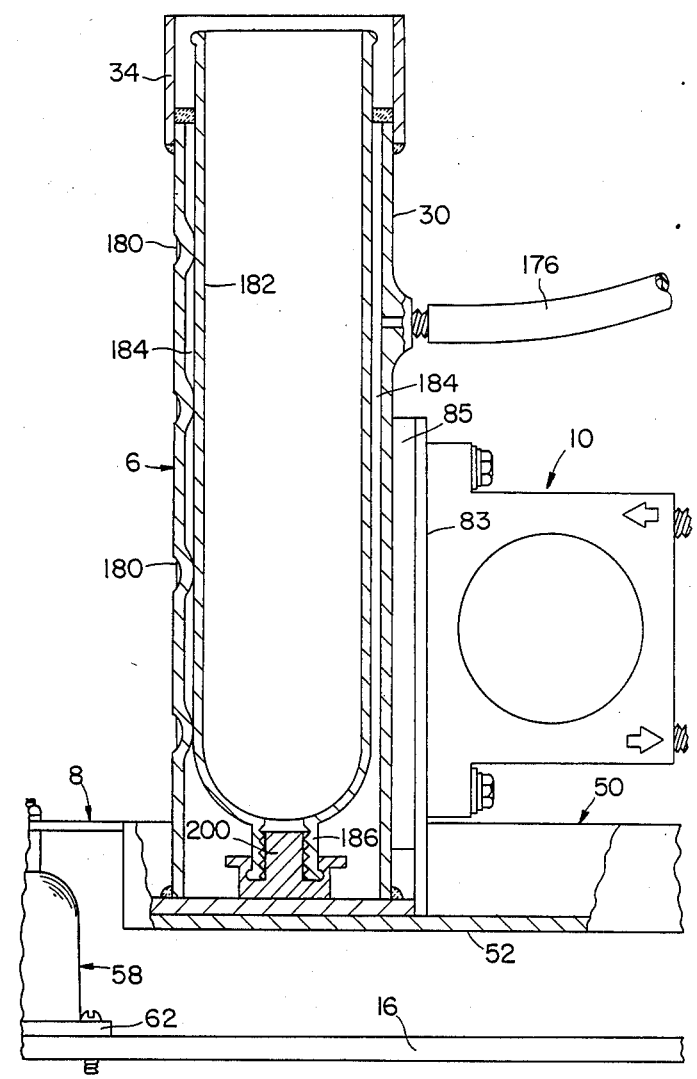
FIG. 6 is a fragmentary view of the gun cartridge holding chamber with a cartridge in place.

The apparatus 2 for preparing bone cement includes a housing 4 and has five (5) main elements therein: (1) a bone cement gun cartridge holding chamber 6; (2) mounting means 8 for mounting said holding chamber 6 for vibration on a bottom plate 16 of housing 4; (3) a fluid operated vibration means 10 fixed to holding chamber 6 for vibrating it; (4) driving fluid conduit means 12 for connecting a driving fluid to said vibration means 10; and (5) conduit means 14 for applying a vacuum to the interior of said holding chamber 6.

The bottom plate 16 of housing 4 includes an upwardly extending control panel 18 and a rubber foot 19 at each corner. A cover 20 is positioned over, and fixed to, said bottom plate 16 by screws 22, with a cut-out portion 24 fitting around said upwardly extending control panel 18. The top of the cover 20 has an opening 26 therein for the top of the cartridge holding chamber 6 to extend therethrough. Cover 20 is also provided with holes 21 on each side thereof to provide for sterilization of the apparatus 2, such as in an autoclave.

The bone cement gun cartridge holding chamber 6 is formed as a cylinder 30 being open at the top and having a closed bottom 32. A cylindrical extension 34 is fixed to the top of the cylinder 30 to provide a larger opening for entry into the holding chamber 6. The upper end of the cylindrical extension 34, which extends through an opening 26 in the top of the cover 20, is adapted to receive a cover 38. Cover 38 can be attached to the top of the cover 20 by attaching means such as a wire, cord, or hinge means. Four rubber snubbers 40 are equally spaced around the interior of the opening 26 and extend radially inwardly of the opening 26 toward the cylindrical extension 34 of the holding chamber 6 to prevent the cylindrical extension 34 from contacting the top of the cover 20 when it is vibrating (to be hereinafter described). Each snubber 40 comprises a small angle member 42 with one arm fixed to the inner surface of the top of the cover 20, and the other arm extending downwardly. A solid rubber member 44 is fixed to each downwardly extending arm of each small angle member 42. Each solid rubber member 44 is formed around a metal core having a threaded member 46 extending externally of the rubber member 44. Each threaded member 46 is threadably mounted to the downwardly extending arm of the small angle member 42.

The mounting means 8 for mounting the holding chamber 6 to bottom plate 16 of housing 4 comprises a mounting plate means 50 with a recessed center portion 52 having flat extending ends 54 and 56. Each corner of each flat extending end 54 and 56 has a vibration mount 58 fixed thereto and connected to the bottom plate 16 of housing 4.

Each vitration mount 58 comprises a hollow metal bell-shaped housing 60 with a flange 62 extending outwardly from the bottom thereof. An inwardly extending flange 64 extends into said bell-shaped housing 60 at a center portion thereof. A rubber core member 66 has a cylindrical diaphragm-type member 68 molded at its outer edge to the inwardly extending flange 64. The center of the rubber core member 66 has an upwardly projecting cylindrical member 70 extending through an opening 72 in the top of the bell-shaped housing 60. A separate metallic member 74 is molded into rubber core member 66 and extends upwardly through the top of the cylindrical member 70. The upper end of each metallic member 74 is threaded and extends through an opening in its cooperating corner of a flat extending end 54 or 56 of mounting plate means 50. A nut 76 is threadably mounted to the upper end of metallic member 74 and fixes the mounting plate means 50 to the cylindrical member 70; and screws 78 extend through flange 62 of each hollow bell-shaped housing 60 and into threaded openings in bottom plate 16.

Fluid operated vibration means 10 includes a housing 80 having an upper flange 82 and a lower flange 84 on one side and a nitrogen inlet connector 86 and an outlet connector 88 positioned on the other side. The vibration means 10 is one having a rotatable member, eccentrically weighted which can be rotated to provide the vibration. The vibration means 10 shown is one having a turbine therein connected to the rotatable member for rotating it. A flow of nitrogen under pressure from a supply 90 is directed to said turbine through inlet connector 86 to provide rotation thereof and the nitrogen is directed from the vibration means 10 through outlet connector 88 to a location remote from the operating area.

The cartridge holding chamber 6 has its closed bottom 32 fixed to the rear part of the recessed center portion 52 of mounting plate means 50, such as by welding. A flat plate 83 extends upwardly adjacent the cartridge holding chamber 6 from within said recessed center portion 52 and is fixed to the cartridge holding chamber 6 through a spacer plate 85. Spacer plate 85 is welded to the cartridge holding chamber 6 and flat plate 83 is welded to the recessed center portion 52 and the spacer plate 85. The upper flange 82 and lower flange 84 of fluid operated vibration means 10 are fixed to the flat plate 83 by bolts 87. When the vibration means 10 vibrates, the vibration is transmitted to the cartridge holding chamber 6.

The nitrogen conduit means 12 for directing nitrogen from the supply 90 to a remote location comprises an inlet connector 92 extending through the bottom of the control panel 18. An external fitting 94, fixed to inlet connector 92, is connected by a conduit 96 to the supply 90. An internal fitting 98, fixed to inlet connector 92, is connected to a connector 99 fixed in an inlet 100 of an on-off valve 102 by a conduit 104. The on-off valve 102 is fixed to the interior of the control panel 18, such as by welding, and has a control lever 106 extending from the exterior of the face of the control panel 18.

Nitrogen flow leaves the on-off valve 102, when the valve is in its "on" position, and is directed to a flow regulator means 108 by a conduit section 110 connected to an elongated manifold 112. Manifold 112 is fixed to the rear of the control panel 18 by an inwardly extending flange 111. Nitrogen flow is directed from elongated manifold 112 by connectors C to three separate flow regulators 114. Flow regulators 114 are of a type where a portion of the flow therethrough can be bypassed to control its outlet flow. The bypass opening from each flow regulator 114 is directed into a manifold 116. The bypass flow directed to the opening in the bottom of each flow regulator 114 is controlled by a separate knob 115. While one specific flow regulating means has been shown, other desired controls can be used.

The main flow from each flow regulator 114 passes through an outlet 118 to the inlet 120 of a common manifold 122 by a conduit 124. Common manifold 122 is fixed to the rear of the control panel 18 by an inwardly extending flange 126. Flange 126 can be fixed by welding or any other well known means. The common manifold 122 has an outlet 128 which is connected to inlet connector 86 of vibration means 10 by conduit 130.

The outlet connector 88 of vibration means 10 is connected by a conduit 131, T-connector 132, and right angle connector 134, to an outlet connector 136 extending through the bottom of the control panel 18 adjacent the inlet connector 92. The bypass flow from manifold 116 is connected by conduit 142 to the extending portion 144 of T-connector 132. This permits the bypass flow to combine with the outlet flow passing through conduit 131 to the exterior of the device. An external fitting 138, fixed to outlet connector 136, has a conduit 140 connected thereto to direct exhaust nitrogen flow to an area removed from said apparatus 2.

The vacuum conduit means 14 for placing a vacuum within cartridge holding chamber 6 from a vacuum source 150 comprises a connector 152 extending through the bottom of the control panel 18. An external fitting 154 fixed to connector 152 is connected by a conduit 156 to the vacuum source 150. A holding chamber 6 has an integral connector 158 extending therefrom with an opening 160 extending therethrough to the interior of the cartridge holding chamber 6.

An internal fitting 162 fixed to connector 152 is connected to a connector 164 fixed in the outlet of a vacuum regulating device 166 by conduit 168. The inlet of the vacuum regulating device 166 is connected to the outlet of an on-off valve 169 by a connector 170. Vacuum regulating device 166 is controlled by a separate knob 167. The on-off valve 169 is fixed to the interior of the control panel 18, such as by welding, and has a control lever 172 extending from the exterior of the face of the control panel 18. A fitting 174, fixed to the inlet of the on-off valve 169, is connected to the integral connector 158 on the holding chamber 6 by a conduit 176.

The vacuum source 150 starts sucking through opening 160 of the cartridge holding chamber 6 when the on-off valve 169 is in its "on" position; this will draw air and gases from the cartridge holding chamber 6 without a cover 38 thereon, and will place a vacuum within the cartridge holding chamber 6 when a cover 38 is in place over the cylindrical extension 34.

The cartridge holding chamber 6 is formed having a plurality of indentations 180 guiding a bone cement gun cartridge 182 into the cartridge holding chamber 6 while spacing it from the walls thereof by space 184. The end of the cement gun cartridge 182, inserted into the cartridge holding chamber 6, has a short projecting internally threaded member 186 for receiving, after bone cement preparation and removal of the cartridge, an elongated nozzle 188 for use in delivering bone cement to a desired operating area, as shown in FIG. 7. For use during bone cement preparation, the short projecting internally threaded member 186 contains a removable plug 200 for preventing the bone cement from leaking into the cartridge holding chamber 6.

While cover 38 can be a plain disc member, with a downwardly extending portion 202 for fitting within cylindrical extension 34 and having an O-ring 204 to provide a seal, the cover 38 can be formed having a mixing rod 206 extending through the center of the cover 38 with a sealing means positioned around the rod 206 within the cover 38. A handle 208 is attached to the external top of the mixing rod 206 and a knob 210 for turning the mixing rod 206 is provided at the end of the handle 208. It can be seen that with this cover, with the mixing rod 206, the bone cement in the gun cartridge 182 can be further mixed under a vacuum.

Steps for one method of operation are set forth below:

(1) set nitrogen supply 90 at a pressure greater than 90 psi (pre-set regulator means 112 provides proper operating flow);
(2) set the vacuum source 150 to provide a vacuum greater than 23 inches of mercury (pre-set regulator means 166 provides proper vacuum);
(3) insert a bone cement gun cartridge 182 with a plug 200 into the cartridge holding chamber 6;
(4) connect vacuum source 150 to cartridge holding chamber 6 by placing on-off valve 169 to its "on" position;
(5) pour liquid catalyst of bone cement into the cement gun cartridge 182;
(6) pour in powder of bone cement for mixing with liquid catalyst in the cement gun cartridge 182, stir with mixing tool until powder is wetted;
(7) turn on nitrogen supply 90 by placing on-off valve 102 in its "on" position, thereby vibrating cement gun cartridge 182;
(8) continue to mix with mixing rod or spatula for 30 seconds until liquid catalyst and powder are properly blended;
(9) place cover 38 on cylindrical extension 34 permitting a vacuum to be formed within the bone cement gun cartridge holding chamber 6;
(10) maintain on-off valve 102 in an "on" position for an additional 30 seconds to provide for deaeration;
(11) place on-off valve 102 to its "off" position, cutting off the nitrogen supply to stop vibration and place on-off valve 169 to its "off" position, cutting off and releasing the vacuum;
(12) remove cover 38 and take out cement gun cartridge 182 with hemostat from cartridge holding chamber 6;
(13) remove plug 200 from cartridge 182 and assemble nozzle 188;
(14) install cartridge 182 into the supporting cylinder of a cement gun for forcing a piston 212 down into the cartridge 182 to force the mixed cement through the nozzle 188 to the operating area—any well known cement gun can be used (See U. S. Pat. No. 2,838,210); and
(15) operate gun to apply force to the piston 212 to deliver cement where desired. A small hole 214, made 0.050 inches in diameter, was used to bleed off trapped air between piston 212 and mixed cement contained within cartridge 182 until piston makes contact with the cement.

I claim:

1. A device for mixing bone cement comprising a housing plate means, a cylinder means being open at the top and having a closed bottom, said cylinder means defining a cylindrical holding chamber, mounting means for mounting said cylinder means on said housing plate means to permit vibration of said cylinder means thereon, vibration means fixedly connected to the side of said cylinder means for vibrating said cylinder means, means for turning said vibration means on and off, a removable cartridge for mixing bone cement being positioned in said cylindrical holding chamber of said cylinder means for vibration therewith, means for spacing said removable cartridge from the wall of said cylindrical holding chamber forming a space therebetween, said removable cartridge being cylindrical and shorter than said cylindrical holding chamber, said removable cartridge being open at its upper end to receive elements of a bone cement for mixing together, a vacuum source, means for turning said vacuum source on and off, conduit means for connecting said vacuum source to said holding chamber through the wall of said cylinder means below the open upper end of said removable cartridge, said conduit means drawing gases from the cylindrical holding chamber from below the open upper end of said removable cartridge through said space when said vacuum source is on.

2. A combination as set forth in claim 1 wherein said removable cartridge includes a lower end with an opening therethrough, a removable plug located in said opening to prevent leaks when mixing elements of a bone cement in said removable cartridge, said opening being located in said lower end of said removable cartridge to receive a nozzle when said cartridge with a mixed bone cement has been removed from said cylindrical holding chamber.

3. A combination as set forth in claim 1 including a cylinder means cover for placement over the open end of the cylinder means when a vacuum is desired therein to provide for deaeration of a mixed bone cement when said cartridge is being vibrated.

4. A combination as set forth in claim 3 wherein said cylinder means cover has a mixing rod extending through the cover, said mixing rod having a handle for turning the mixing rod and mixing a bone cement while it is under a vacuum and said cartridge is being vibrated.

5. A combination as set forth in claim 1 wherein said mounting means comprises a mounting plate means, said cylinder means being fixed at its bottom to said mounting plate means, said mounting means including vibration mounts connected between said mounting plate means and said housing plate means, said mounting plate means being vibrated by said cylinder means on said vibration mounts.

6. A combination as set forth in claim 1 including said mounting means providing the only supporting connection of said cylinder means on said housing plate means, said vibration means being fixedly connected to the side of said cylinder means between its top and bottom.

7. A device for mixing bone cement comprising a housing plate means, one cylinder means being open at the top and having a closed bottom, said cylinder means defining a single cylindrical holding chamber, a mounting plate means for said one cylinder means, means fixing the bottom of said one cylinder means to said mounting plate means, vibration mounts connected between said mounting plate means and said housing plate means to support said mounting plate means with said one cylinder means and permit vibration of said one cylinder means, vibration means fixedly connected to the side of said one cylinder means between its top and bottom for vibrating said cylinder means, means for turning said vibration means on and off, a removable cartridge for mixing bone cement being positioned in said cylindrical holding chamber of said cylinder means for vibration therewith, means for spacing said removable cartridge from the wall of said cylindrical holding chamber forming a space therebetween, said removable cartridge being cylindrical and shorter than said cylindrical holding chamber, said removable cartridge being open at its upper end to receive liquid and powder elements of a bone cement for mixing while said cylinder means is open, said vibration means being used to vibrate said cylinder means and said removable cartridge while said liquid and powder elements of a bone cement are being mixed, a vacuum source, means for turning said vacuum source on and off, conduit means for connecting said vacuum source to said holding chamber through the wall of said cylinder means below the open upper end of said removable cartridge, said conduit means drawing gases from the cylindrical holding chamber from below the open upper end of said removable cartridge through said space when said vacuum source is on, a cover for placement over the open end of the cylinder means when a vacuum is desired therein, said vibration means being used to vibrate said removable cartridge when under a vacuum to deaerate said mixed bone cement.

8. A device for use in an operating room to prepare bone cement in a removable cartridge, a housing plate means, a cylindrical holding device being open at the top and closed at the bottom, said cylindrical holding device having a cylindrical holding chamber, mounting means for mounting said cylindrical holding device to said housing plate means to permit vibration of said cylindrical holding device, a cylindrical cartridge for preparing a bone cement for use, said cartridge being positioned in said cylindrical holding chamber and having an open upper end for receiving the elements of a bone cement for mixing, vibration means connected to the side of said cylindrical holding device for vibrating said device and said cartridge, means for turning said vibration means on and off, means for spacing said cartridge from the wall of said cylindrical holding chamber to permit gas flow therebetween when said bone cement elements are being placed in said cartridge and mixed, said cartridge being cylindrical and shorter than said holding chamber, a vacuum source, means for turning said vacuum source on and off, conduit means for connecting said vacuum source to said holding chamber through said cylindrical holding device below the open top of said cartridge and open top of said cylindrical holding device, said conduit means drawing gases formed by the mixing of the bone cement elements from the cylindrical holding chamber to prevent them from entering an operating room.

9. A combination as set forth in claim 8 including a cylindrical holding chamber cover for placement over the open end of the cylindrical holding chamber when a vacuum is desired therein to provide for deaeration of a mixed bone cement when said cartridge is being vibrated.

10. A combination as set forth in claim 9 wherein said cylindrical holding chamber cover has a mixing rod extending through the cover, said mixing rod having a handle for turning the mixing rod and mixing a bone cement while it is under a vacuum and said cartridge is being vibrated.

* * * * *